US011332421B2

(12) United States Patent
Peitz et al.

(10) Patent No.: US 11,332,421 B2
(45) Date of Patent: May 17, 2022

(54) PROCESS FOR OLIGOMERIZATION OF OLEFINS WITH OPTIMIZED DISTILLATION

(71) Applicant: Evonik Operations GmbH, Essen (DE)

(72) Inventors: Stephan Peitz, Oer-Erkenschwick (DE); Guido Stochniol, Haltern am See (DE); Armin Matthias Rix, Marl (DE); Niklas Paul, Marl (DE); Tatina Valèrie Six, Dortmund (DE)

(73) Assignee: Evonik Operations GmbH, Essen (DE)

( * ) Notice: Subject to any disclaimer, the term of this patent is extended or adjusted under 35 U.S.C. 154(b) by 64 days.

(21) Appl. No.: 16/991,436

(22) Filed: Aug. 12, 2020

(65) Prior Publication Data

US 2021/0053892 A1 Feb. 25, 2021

(30) Foreign Application Priority Data

Aug. 21, 2019 (EP) ..................... 19192737

(51) Int. Cl.
*C07C 7/04* (2006.01)
*B01D 3/00* (2006.01)
*B01D 3/14* (2006.01)
*B01J 23/78* (2006.01)
*C07C 2/10* (2006.01)

(52) U.S. Cl.
CPC ............... *C07C 7/04* (2013.01); *B01D 3/009* (2013.01); *B01D 3/143* (2013.01); *B01J 23/78* (2013.01); *C07C 2/10* (2013.01); *C07C 2523/78* (2013.01)

(58) Field of Classification Search
CPC ......... C07C 7/04; C07C 2/10; C07C 2523/78; C07C 2523/755; C07C 7/005; C07C 2/12; B01D 3/009; B01D 3/143; B01J 23/78
See application file for complete search history.

(56) References Cited

U.S. PATENT DOCUMENTS

| | | | |
|---|---|---|---|
| 7,161,054 B2 | 1/2007 | Heidemann et al. | |
| 7,939,597 B2 | 5/2011 | Bub et al. | |
| 8,198,481 B2 | 6/2012 | Kuppinger et al. | |
| 8,254,945 B2 | 8/2012 | Lee et al. | |
| 8,258,249 B2 | 9/2012 | Bub et al. | |
| 8,293,941 B2 | 10/2012 | Kuppinger et al. | |
| 8,481,784 B2 | 7/2013 | Kuppinger et al. | |
| 8,895,683 B2 | 11/2014 | Kuppinger et al. | |
| 9,856,184 B2 | 1/2018 | Stochniol et al. | |
| 10,189,755 B2 | 1/2019 | Reeker et al. | |
| 10,196,327 B2 | 2/2019 | Stochniol et al. | |
| 10,227,279 B2 | 3/2019 | Stochniol et al. | |
| 10,633,302 B2 | 4/2020 | Nadolny et al. | |
| 2004/0181105 A1 | 9/2004 | Heidemann et al. | |
| 2006/0276334 A1 | 12/2006 | Balduf et al. | |
| 2009/0068440 A1 | 3/2009 | Bub et al. | |
| 2010/0312031 A1 | 12/2010 | Heidemann | |
| 2016/0152527 A1* | 6/2016 | Peitz ............ | C07C 45/505 549/313 |
| 2019/0283003 A1 | 9/2019 | Nadolny et al. | |
| 2019/0283004 A1 | 9/2019 | Nadolny et al. | |
| 2019/0283005 A1 | 9/2019 | Nadolny et al. | |
| 2019/0283006 A1 | 9/2019 | Nadolny et al. | |
| 2020/0216376 A1 | 7/2020 | Peitz et al. | |
| 2020/0216763 A1 | 7/2020 | Peitz et al. | |

FOREIGN PATENT DOCUMENTS

EP 1 457 475 A2 9/2004
WO 2009/095411 A1 8/2009

OTHER PUBLICATIONS

Peitz et al., U.S. Appl. No. 16/991,327, filed Aug. 12, 2020 (unpublished application not included).
GC Search Report completed on Sep. 12, 2021 in Application No. GC 2020-40316 (2 pages).
European Search Report dated Dec. 18, 2020 in EP 20190854.8 (7 pages).

* cited by examiner

*Primary Examiner* — Ali Z Fadhel

(74) *Attorney, Agent, or Firm* — Taylor English Duma LLP; Philip P. McCann

(57) ABSTRACT

The present invention relates to a process for oligomerization of C2- to C8-olefins in at least two reaction stages, wherein in the last distillation column the reaction mixture is fractionated such that only very small amounts of the reactant olefins and the analogous alkanes remain in the bottom of the distillation column.

19 Claims, No Drawings

PROCESS FOR OLIGOMERIZATION OF OLEFINS WITH OPTIMIZED DISTILLATION

CROSS REFERENCE TO RELATED APPLICATIONS

This application is a 35 U.S.C. § 119 patent application which claims the benefit of European Application No. 19192737.5 filed Aug. 21, 2019, which is incorporated herein by reference in its entirety.

FIELD

The present invention provides a process for oligomerization of C2- to C8-olefins in at least two reaction stages, wherein in the last distillation column the reaction mixture is fractionated such that only very small amounts of the reactant olefins and the analogous alkanes remain in the bottom of the distillation column.

BACKGROUND

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a two-phase catalyst system.

Processes for oligomerization of olefins are well known in the prior art and are used on a large industrial scale. Production quantities amount to several thousand kilotons per year in Germany alone. To ensure the highest possible conversions and, as far as possible, continuous operation of oligomerization processes, industrial plants usually comprise not just one but at least two serially connected reaction stages, each comprising at least one reactor. As a result, the oligomerization process can be kept in operation even in the case of failure of one reaction stage.

The reaction stage further comprises at least one distillation column to separate the oligomers formed from the olefins employed. The input olefin-containing stream is removed overhead as distillate and the oligomer depleted in input olefins is discharged via the column bottom. It is known that inadequate separation of the reactant olefins from the formed oligomers in the bottoms has the result that the purity of the oligomers in subsequent process steps, for example in the separation of the oligomers from high-boiling byproducts, cannot be maintained and can therefore lead to problems.

SUMMARY

The problem addressed by the present invention was that of providing a process for oligomerization of olefins which does not suffer from the abovementioned problems but also entails the lowest possible capital costs for the construction of a multistage oligomerization, especially in terms of the columns. In this regard, costs increase with each additional separation stage. The problem addressed by the present invention was solved with the process for oligomerization according to Claim 1. Preferred configurations are specified in the dependent claims.

DETAILED DESCRIPTION

The process according to the invention is a process for oligomerization of C2- to C8-olefins, preferably C3- to C6-olefins, more preferably C3- to C5-olefins and particularly preferably C4-olefins, in at least two serially connected reaction stages, each of which comprise at least one reactor and at least one distillation column, wherein an input mixture containing at least the C2- to C8-olefins as reactant olefins and a proportion of >10% by weight of their analogous alkanes and preferably up to 50% by weight of their analogous alkanes is subjected to oligomerization in the at least one reactor using a heterogeneous catalyst with a reactant olefin conversion of 60 to 95%, preferably 70 to 93%, particularly preferably 80 to 92%, and the reaction mixture obtained from the at least one reactor is distilled in the at least one distillation column to separate the formed oligomers from the residual reaction mixture containing at least the unconverted reactant olefins and the alkanes and forming the distillate from the distillation column, wherein the distillate formed in the at least one distillation column is at least partially passed to the reactor(s) of the same or preceding reaction stage, characterized in that the bottom output or the bottom outputs from the distillation column(s) are passed from the respective reaction stages to the last distillation column of the last reaction stage and the concentration of the reactant olefins and/or the concentration of the alkanes in the bottom of the last distillation column is <200 ppmw, preferably <150 ppmw, particularly preferably <100 ppmw.

In the bottom or in the bottoms of the preceding distillation column(s), the concentration of the reactant olefins and/or the concentration of the alkanes may be >200 ppmw, preferably at most 2% by weight, by contrast.

In the context of the present invention, the term "reaction stage" means a plant section comprising one or more reactor(s) and one or more distillation column(s) downstream of the reactor. In a preferred embodiment, only one distillation column is present per reaction stage. In the distillation columns especially the produced oligomers are separated from the residual output stream of the reactor which comprises, for example, alkanes and unconverted olefins. The oligomers are higher boiling than the unconverted olefins and other substances present in the output stream from the reactor and are therefore enriched in the bottom of the distillation column while the lower boiling unconverted olefins and analogous alkanes optionally present in the input stream are removed from the distillation column overhead and enriched in the distillate. Typical process-engineering units which can be incorporated in the reaction stages, such as for example preheaters for the feed, heat exchangers or the like are not listed separately here, but are familiar to those skilled in the art.

The typically employed input mixtures for the oligomerization consist to a significant proportion of inert alkanes, here more than 10% by weight and preferably up to 50% by weight. The mass flow of alkanes remains constant over the entire multistage oligomerization on account of its inertness. Economic operation of an oligomerization is possible only with conversions of olefins of <100% since the multistage nature of the plant causes the olefin concentration in the feed of the respective subsequent stage to become ever smaller while the mass flow of alkanes remains constant, this having a markedly retarding effect on the kinetics of the oligomerization. It is accordingly provided according to the present invention that the reactant olefin conversion is limited to a range of 60% to 95%, preferably 70% to 93%, particularly preferably 80% to 92%.

In order to achieve a sufficiently high conversion of olefins over the entire process despite the negative development of the kinetics of the reaction from stage to stage, an at least partial recycling of the distillate from the distillation column into the reactor feed is carried out. The at least partial recycling of the distillate to a preceding reactor is performed to allow the remaining butenes sufficient residence time for the reaction. The reflux establishes a particular ratio of recycle (=recycled distillate) to fresh feed which is also referred to as the recycle-feed ratio. In the present process the recycle-fresh feed ratio is preferably between 0.1 and 5, particularly preferably between 0.1 and 3, for each of the reaction stages present.

It has surprisingly been found that a virtually reactant olefin-free bottoms fraction is necessary only in the last distillation column of an oligomerization comprising at least two stages. It is thus possible to save energy also in existing plants since it is no longer necessary to separate all reactant olefins from the column bottom of all distillation columns. Distillation columns to be newly constructed, except the last distillation column, can be made smaller since the separation performance in the column bottom need not be at the level of complete removal of the reactant components. On the contrary, a reactant olefin concentration of >200 ppmw, preferably up to at most 2% by weight, may be present in the bottom or the bottoms of the preceding distillation column(s) for separation of the oligomers from the reactant olefins. These bottom outputs are passed to the last distillation column of the last reactor stage and subjected to further purification therein. The bottom output/bottom outputs may be passed into the last column via a separate feed port or else passed into the column in admixture together with the output from the last reactor.

The concentration of the reactant olefins and/or the concentration of the alkanes in the bottom of the last distillation column is <200 ppmw, preferably <150 ppmw, particularly preferably <100 ppmw.

In a preferred embodiment of the present invention, the concentration of the oligomers in the distillate from the last distillation column of the last reaction stage may additionally be <100 ppmw, preferably <80 ppmw, particularly preferably <50 ppmw, while the distillate(s) from the preceding distillation column(s) have a concentration of the oligomers of >200 ppmw and preferably at most 2% by weight. The distillate formed in the at least one distillation column is at least partially passed back to the reactor(s) of the same or preceding reaction stage, preferably of the same reaction stage.

The process according to the invention comprises at least two reaction stages. In a preferred embodiment, the process for oligomerization comprises not more than five reaction stages. A process regime comprising three or four reaction stages is especially preferred. Each of these reaction stages independently of one another comprises one or more reactors and one or more subsequent distillation columns to separate the formed oligomers from the residual output stream from the reactor. However, it is also conceivable for one of the reaction stages to comprise two or more reactors while a preceding or subsequent reaction stage comprises only one reactor.

The oligomerization of olefins is an exothermic reaction, i.e. a reaction which liberates heat. In order to keep the oligomerization temperature in a desired range, the reactors may be cooled using a cooling medium to remove a large portion (more than 60%) of the total liberated heat. This corresponds to an isothermal operating mode. In order to utilize the liberated heat for subsequent processes, cooling may be partially or completely dispensed with. If the reactors are not actively cooled this is referred to as an adiabatic operating mode. The heat liberated during the oligomerization is removed by the discharging of the product stream from the reactor and accordingly utilized in the distillation column. The subsequent distillation column thus requires less energy for evaporation and the distillation can thus be performed in a more energy-saving manner.

The reactor or reactors in the respective reaction stages of the process according to the invention may be operated isothermally or adiabatically. In a preferred embodiment, only the reactor(s) of the last reaction stage are operated adiabatically while all other reactors of the preceding reaction stage(s) are actively cooled. A cooling medium known to those skilled in the art, for example cooling water, may be employed. In a preferred embodiment, the temperature increase in the reactor despite cooling should not exceed 5 K. This corresponds to an isothermal operating mode of the reactors. Based on a cooling power of 100% for the reactor(s) in the first reaction stage, the cooling power in the reactor(s) of the subsequent reaction stages is less than 100% but, except in the last reaction stage, not 0%.

In a very preferred embodiment, when three reaction stages are present, the cooling power for the reactor(s) of the first reaction stage is 100% and for the reactor(s) of the second reaction stage is 10 to 60%, wherein the reactor of the third and last reaction stage is operated adiabatically. In a further very preferred embodiment, when four reaction stages are present, the cooling power for the reactor(s) of the first reaction stage is 100%, for the reactor(s) of the second reaction stage is 40 to 60% and for the reactor(s) of the third reaction stage 10 to 30%, wherein the reactor of the fourth and last reaction stage is operated adiabatically.

In a preferred embodiment, the heat absorbed by the cooling medium during the cooling in the reaction stages preceding the adiabatically operated reaction stage may be used to heat one or more of the feed streams, preferably all feed streams, to the individual reaction stages, preferably to a temperature T>50° C. This can be carried out in a manner known to those skilled in the art, particularly by using a heat exchanger. Thus, the heat formed during the reaction and absorbed by the cooling medium during cooling can still be used for the further process, which is advantageous from an economic and ecological point of view.

According to the invention the respective feed stream composed of the input mixture is oligomerized in the at least one reactor in the individual reaction stages and the obtained product mixture is in each case passed to a distillation column in which the reactant olefins are separated overhead as distillate from the residual product mixture. Depending on the reaction stage, the distillate may then be at least partially passed to the respective next reaction stage as a feed stream and optionally partially recycled to the reactor(s) of the same or a preceding reaction stage. In the last reaction stage, i.e. the second, third, fourth, fifth or subsequent reaction stage, the distillate may also be at least partially discharged from the process. If the distillate from the last distillation column of the last reaction stage is discharged from the presently disclosed process, it may be used as a synthesis raw material for further processes (for example hydroformylation, carbon source for arcs in acetylene production), as combustion gas or, after full hydrogenation to the alkanes, as propellant gas, as cooking gas or the like.

The conditions of the distillation, i.e. temperature and pressure for example, are typically determined by the set-up (column height, number of trays, type of trays/packing, spacings etc.). The separation properties of the distillation may also be controlled during operation via the temperature distribution and/or the heat supply into the column and the reflux in the distillate. Separation properties may also be adjusted by alteration of the pressure within a certain range. Precise settings therefore cannot be defined superordinately to and independently of the set-up of the distillation column, which is, however, known to those skilled in the art.

The input mixture for the process according to the invention contains at least the C2- to C8-olefins, preferably C3- to C6-olefins, more preferably C3- to C5-olefins, particularly preferably C4-olefins and a proportion of >10% by weight of their analogous alkanes and preferably up to 50% by weight of their analogous alkanes. Suitable olefins include α-olefins, n-olefins and cycloalkenes, preferably n-olefins. In a preferred embodiment, the olefin is n-butene. In this case the analogous alkane is butane or isobutane.

The olefins are typically used as reactants not in pure form but in industrially available mixtures. The term input mixture used additionally in this invention is therefore to be understood as encompassing any type of mixtures containing the relevant olefins to be oligomerized in an amount which allows economic performance of the oligomerization. The input mixtures used in accordance with the invention preferably contain practically no further unsaturated compounds and polyunsaturated compounds such as dienes or acetylene derivatives. It is preferable to employ input mixtures containing less than 5% by weight, in particular less than 2% by weight, of branched olefins based on the olefin proportion.

Propylene is produced on a large industrial scale by cracking of naphtha and is a commodity chemical which is readily available. C5 olefins are present in light petroleum fractions from refineries or crackers. Industrial mixtures containing linear C4 olefins are light petroleum fractions from refineries, C4 fractions from FC crackers or steam crackers, mixtures from Fischer-Tropsch syntheses, mixtures from the dehydrogenation of butanes and mixtures formed by metathesis or from other industrial processes. Mixtures of linear butenes suitable for the process according to the invention are obtainable from the C4 fraction of a steam cracker for example. Butadiene is removed in a first step. This is accomplished either by extraction (extractive distillation) of the butadiene or by selective hydrogenation thereof. In both cases a virtually butadiene-free C4-cut is obtained, so-called raffinate 1. In the second step, isobutene is removed from the C4 stream, for example by production of MTBE by reaction with methanol. The now isobutene-free and butadiene-free C4 cut, referred to as raffinate II, comprises the linear butenes and any butanes. If this then also undergoes removal of at least a portion of the 1-butene present, so-called raffinate III is obtained.

In a preferred embodiment, C4-olefin-containing streams are supplied as the input mixture in the process according to the invention. Suitable olefin mixtures are in particular raffinate II and raffinate III.

The use of n-butenes as reactant olefins results in the following particularly preferred process: Process for oligomerization of n-butenes in at least two serially connected reaction stages, each of which comprise at least one reactor and at least one distillation column, wherein an input mixture containing at least the n-butenes as reactant olefins and a proportion of >10% by weight of C4-alkanes and preferably up to 50% by weight of C4-alkanes is subjected to oligomerization in the at least one reactor using a heterogeneous catalyst with a reactant olefin conversion of 60 to 95%, preferably 70 to 93%, particularly preferably 80 to 92%, and the reaction mixture obtained from the at least one reactor is distilled in the at least one distillation column to separate the formed butene oligomers (octenes and higher oligomers) from the residual reaction mixture containing at least unconverted n-butenes and the C4-alkanes and forming the distillate from the distillation column, wherein the distillate formed in the at least one distillation column is at least partially passed to the reactor(s) of the same or preceding reaction stage, characterized in that the bottom output or the bottom outputs from the distillation column(s) are passed from the respective reaction stages to the last distillation column of the last reaction stage and the concentration of the butenes and/or the concentration of the further C4-compounds in the bottom of the last distillation column of the last reaction stage is <200 ppmw, preferably <150 ppmw, particularly preferably <100 ppmw.

In the bottom or in the bottoms of the preceding distillation column(s) the concentration of the butenes and/or the concentration of the further C4-compounds may be >200 ppmw, preferably at most 2% by weight.

Employable reactors for the respective reaction stages include all reactor known to those skilled in the art which are suitable for oligomerization, for example tubular reactors, tube bundle reactors, settler-riser reactors or slurry reactors. Preference is given to tubular reactors and/or tube bundle reactors. If a reaction stage has two or more reactors the reactors may be identical or different to one another. The reactors in a reaction stage may also vary in their construction or their configuration. For example the first reactor in a reaction stage may have a larger volume than the subsequent reactor in the same reaction stage. It is likewise possible for the reactors in the individual reaction stages to be identical or different to one another. Here too it is possible for the reactors in the individual reaction stages to differ in their construction or their configuration. The reactor in the first reaction stage may have a larger volume than one or all reactors in the subsequent reaction stages for example.

The reactor or reactors of the individual reaction stages each contain a heterogeneous oligomerization catalyst for performing the oligomerization. The employed heterogeneous oligomerization catalyst is especially in the form of a granulate, an extrudate or in tablet form.

The (heterogeneous) oligomerization catalysts may comprise a nickel compound, preferably nickel oxide, on an aluminosilicate support material. It is particularly preferred for the catalysts used in the process according to the invention to contain less than 0.5% by weight, preferably less than 0.1% by weight, particularly preferably less than 0.01% by weight, of titanium dioxide and zirconium dioxide based on the total composition of the oligomerization catalyst. The support material may be an amorphous, mesoporous aluminosilicate, a crystalline, microporous aluminosilicate or an aluminosilicate having amorphous and crystalline phases. In the context of the present invention "amorphous" is to be understood as meaning the property of a solid which results from the fact that, in contrast to crystalline solids, the solid has no crystal structure, i.e. no long-range order.

It is preferable according to the invention when the oligomerization catalyst has a composition of 15% to 40% by weight, preferably 15% to 30% by weight, of NiO, 5% to 30% by weight of $Al_2O_3$, 55% to 80% by weight of $SiO_2$ and 0.01% to 2.5% by weight, preferably 0.05% to 2% by weight, of an alkali metal oxide, preferably sodium oxide. The figures are based on a total composition of 100% by weight. The oligomerization catalyst is substantially free from titanium dioxide and zirconium dioxide, the oligomerization catalyst in particular comprising less than 0.5% by weight, preferably less than 0.1% by weight, particularly preferably less than 0.01% by weight of titanium dioxide and zirconium dioxide in its total composition.

The oligomerization catalyst preferably has a specific surface area (calculated according to BET) of 150 to 700 m$^2$/g, more preferably of 190 to 600 m$^2$/g, particularly preferably of 220 to 550 m$^2$/g. The BET surface area is measured by nitrogen physisorption according to DIN ISO 9277 (2014-01 version).

The oligomerization catalysts present in the individual reactors in the reaction stages may each independently of one another be selected from the abovementioned substances. The individual oligomerization catalysts in the reactors are not always exactly identical but rather differ from one another in composition, possibly only to a limited extent. A further reason for this is that even if each reactor contains a completely identical catalyst composition when the process according to the invention is first brought online, this composition changes over time during operation due to a multiplicity of effects over the years (regenerated catalyst behaves differently to virgin catalysts, abrasion during operation, different rate of aging and/or poisoning, etc.).

An oligomerization catalyst may be produced by the known processes of impregnation, wherein the support material is treated with a solution of a transition metal compound, especially a nickel compound, and then calcined, or coprecipitation, wherein the entire catalyst composition is precipitated from a single, usually aqueous, solution. The oligomerization catalyst may also be produced by other processes familiar to those skilled in the art.

The oligomerization may be performed at a temperature in the range from 50° C. to 200° C., by preference 60° C. to 180° C., preferably in the range from 60° C. to 130° C. in each of the reaction stages present. The pressure may be from 10 to 70 bar, preferably 20 to 55 bar, in each of the reaction stages present. In a preferred embodiment of the present invention the oligomerization is carried out in each reaction stage in the liquid phase. If the oligomerization is to be carried out in the liquid phase, the parameters pressure and temperature therefor must be chosen such that the input mixture (the employed olefins or olefin mixtures) is in the liquid phase.

The weight-based space velocities (reactant mass per unit catalyst mass per unit time; weight hourly space velocity (WHSV)) are in the range between 1 g of reactant per g of catalyst and per h (=1 h$^{-1}$) and 190 h$^{-1}$, preferably between 2 h$^{-1}$ and 35 h$^{-1}$, particularly preferably between 3 h$^{-1}$ and 25 h$^{-1}$.

Particularly when using a catalyst comprising a nickel compound, preferably nickel oxide, on an aluminosilicate support material, the degree of dimerization (also referred to as "percentage selectivity based on dimerization") after the oligomerization is at least 60%, more preferably at least 75%, particularly preferably at least 80%, based on the converted reactant.

The linearity of an oligomerization product or of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a C8 fraction. The lower the ISO index, the more linear the structure of the molecules in the respective fraction. The ISO index is calculated according to the following general formula, wherein the proportion of the individual dimer fractions is based on the total dimer fraction:

$$\frac{\left(\begin{array}{l}\text{simply branched dimers}(\% \text{ by weight}) + \\ 2 \times \text{doubly branched dimers }(\% \text{ by weight})\end{array}\right)}{100}$$

Accordingly, a dimer mixture having an ISO index of 1.0 has an average of precisely one methyl branch per dimeric molecule.

The ISO index of the product from the oligomerization process according to the invention is preferably 0.8 to 1.2, particularly preferably 0.8 to 1.15.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a C9-alcohol mixture by hydrogenation. The $C_9$ acid mixture may be used for producing lubricants or siccatives. The C9 alcohol mixture is a precursor for the production of plasticizers, especially dinonyl phthalates, or DINCH and DINCD.

The invention claimed is:

1. A process for oligomerization of from C2- to C8-olefins in at least two serially connected reaction stages, each of which comprise at least one reactor and at least one distillation column, comprising
    oligomerizing an input mixture containing at least the from C2- to C8-olefins as reactant olefins and a proportion of >10% by weight of their analogous alkanes in the at least one reactor using a heterogeneous catalyst with a reactant olefin conversion of 60 to 95%, and
    distilling the reaction mixture obtained from the at least one reactor in the at least one distillation column to separate the formed oligomers from a distillate comprising at least the unconverted reactant olefins and the alkanes, wherein the distillate formed in the at least one distillation column is at least partially passed to the reactor(s) of the same or preceding reaction stage as a recycle,
    wherein the bottom output or the bottom outputs from the distillation column(s) are passed from the respective reaction stages to the last distillation column of the last reaction stage and the concentration of the reactant olefins and/or the concentration of the alkanes in the bottom of the last distillation column is <200 ppmw, and
    wherein based on a cooling power of 100% for the reactor(s) in the first reaction stage, the cooling power in the reactor(s) of the subsequent reaction stages is less than 100%, but 0% only in the last reaction stage.

2. The process for oligomerization according to claim 1, wherein in the bottom or in the bottoms of the preceding distillation column(s) the concentration of the reactant olefins and/or the concentration of the alkanes is >200 ppmw.

3. The process for oligomerization according to claim 1, wherein the concentration of the reactant olefins and/or the concentration of the alkanes in the bottom of the last distillation column is <150 ppmw.

4. The process for oligomerization according to claim 1, wherein the concentration of the reactant olefins and/or the concentration of the alkanes in the bottom of the last distillation column is <100 ppmw.

5. The process according to claim 1, wherein the reactors of the individual reaction stages employ an oligomerization catalyst which comprises a nickel compound on an aluminosilicate support material.

6. The process according to claim 5, wherein the catalyst contains less than 0.5% by weight of titanium dioxide and zirconium dioxide in its overall composition.

7. The process for oligomerization according to claim 5, wherein the oligomerization catalyst in the reactors of the individual reaction stages has a composition of from 15% to 40% by weight of NiO, from 5% to 30% by weight of $Al_2O_3$, from 55% to 80% by weight of $SiO_2$ and from 0.01% to 2.5% by weight of an alkali metal oxide.

8. The process for oligomerization according to claim 1, wherein the oligomerization in each of the reaction stages present is carried out at a temperature in the range from 50° C. to 200° C.

9. The process for oligomerization according to claim 1, wherein the pressure in the oligomerization of each of the reaction stages present is from 10 to 70 bar.

10. The process for oligomerization according to claim 1, wherein the process is a process for oligomerization of from C3- to C6-olefins.

11. The process for oligomerization according to claim 10, wherein the process is a process for oligomerization of from C3- to C5-olefins.

12. The process for oligomerization according to claim 10, wherein the process is a process for oligomerization of C4-olefins.

13. The process according to claim 10, wherein the recycle-to-fresh feed ratio for each of the reaction stages present is between 0.1 and 5.

14. The process according to claim 10, wherein the input mixture contains up to 50% by weight of alkanes.

15. The process for oligomerization according to claim 10, wherein an input mixture containing the from C2- to C8-olefins as reactant olefins and a proportion of >10% by weight of alkanes is subjected to oligomerization in the at least one reactor using a heterogeneous catalyst with a reactant olefin conversion of from 70 to 93%.

16. The process for oligomerization according to claim 10, wherein an input mixture containing the from C2- to C8-olefins as reactant olefins and a proportion of >10% by weight of alkanes is subjected to oligomerization in the at least one reactor using a heterogeneous catalyst with a reactant olefin conversion of from 80 to 92%.

17. The process for oligomerization according to any of claim 2, wherein the reactors of the individual reaction stages employ an oligomerization catalyst which comprises a nickel compound on an aluminosilicate support material.

18. The process according to claim 17, wherein the catalyst contains less than 0.5% by weight of titanium dioxide and zirconium dioxide in its overall composition.

19. The process according to claim 10, wherein the recycle-to-fresh feed ratio for each of the reaction stages present is between 0.1 and 3.

* * * * *